United States Patent [19]

Martin

[11] Patent Number: 4,682,978
[45] Date of Patent: Jul. 28, 1987

[54] DUAL LUMEN CANNULA

[75] Inventor: Geoffrey S. Martin, Mississauga, Canada

[73] Assignee: Vas-Cath of Canada Limited, Mississauga, Canada

[21] Appl. No.: 734,225

[22] Filed: May 15, 1985

[30] Foreign Application Priority Data

May 24, 1984 [CA] Canada .................................. 454986

[51] Int. Cl.[4] .............................................. A61M 5/00
[52] U.S. Cl. ...................................... 604/43; 604/283
[58] Field of Search ........................ 604/43, 44, 45, 53, 604/93, 173, 264, 280–284

[56] References Cited

U.S. PATENT DOCUMENTS

| D. 272,651 | 2/1984 | Mahurkar | 604/44 |
| 4,027,668 | 6/1977 | Dunn | 604/43 |
| 4,214,593 | 7/1980 | Imbruce et al. | 604/45 |
| 4,352,354 | 10/1982 | Ujihara | 604/43 |
| 4,451,252 | 5/1984 | Martin | 604/43 |
| 4,543,087 | 9/1985 | Sommercorn et al. | 604/43 |
| 4,619,643 | 10/1986 | Bai | 604/164 |

Primary Examiner—C. Fred Rosenbaum
Assistant Examiner—Gene B. Kartchner
Attorney, Agent, or Firm—Rogers & Scott

[57] ABSTRACT

A dual lumen cannula for use in haemodialysis has an improved leading end to facilitate insertion and an improved coupling for connection to blood extraction and return tubes. The improved leading end has a conical tip centered on the longitudinal axis of the cannula and, in the leading end, the extraction lumen is blanked off by using an insert to prevent blood flow downstream of the extraction lumen, and to minimize blood stagnation and damage. The improved coupling is generally Y-shaped and the extraction and return lumens of the cannula terminate in conical shaped ends which receive extraction and return tubes with similar shaped ends. The ends of the extraction and return tubes have minimal thickness so that when inserted the interior surfaces of the cannula lumens and the tubes merge smoothly to minimize blood impact problems. Methods of manufacturing the tip and a Y-shaped connecting piece for connecting the dual lumen cannula to tubing are also described.

3 Claims, 20 Drawing Figures

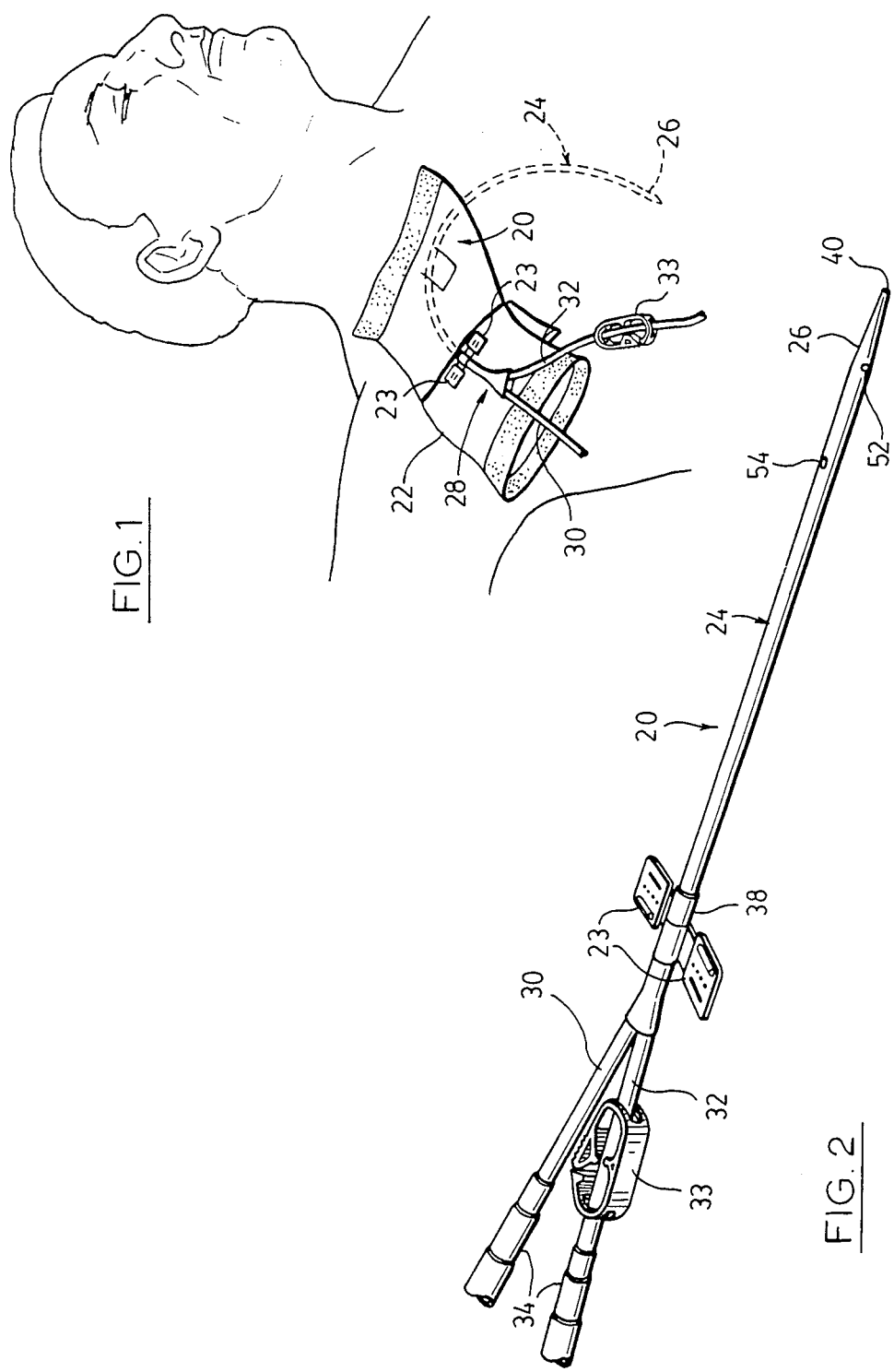

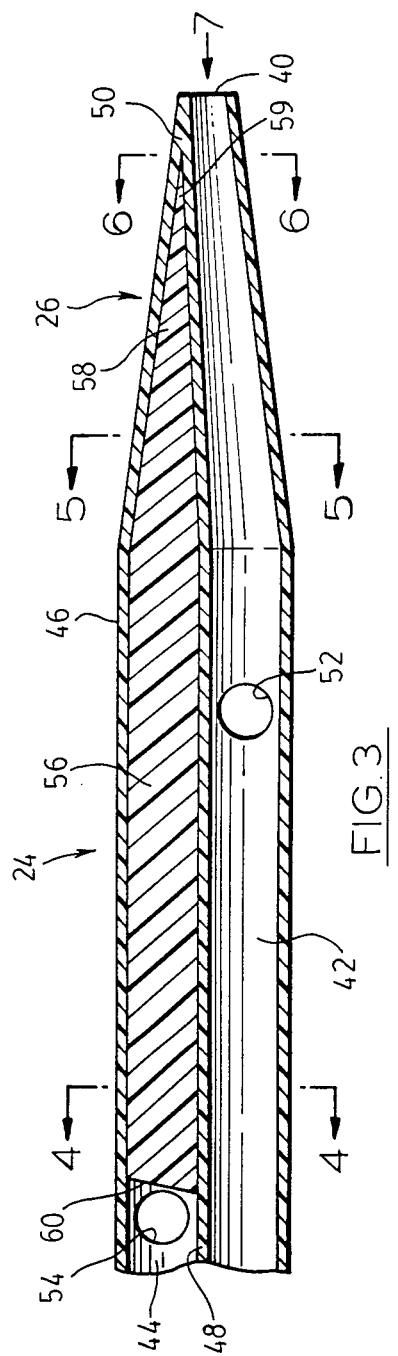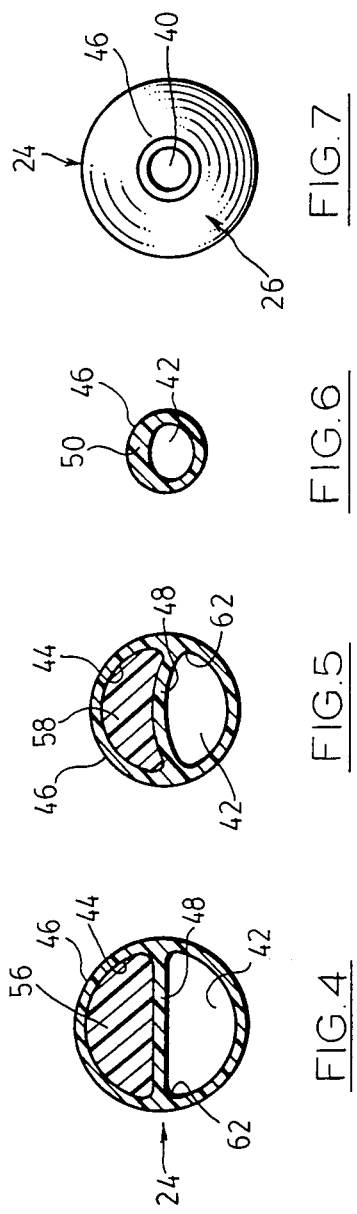

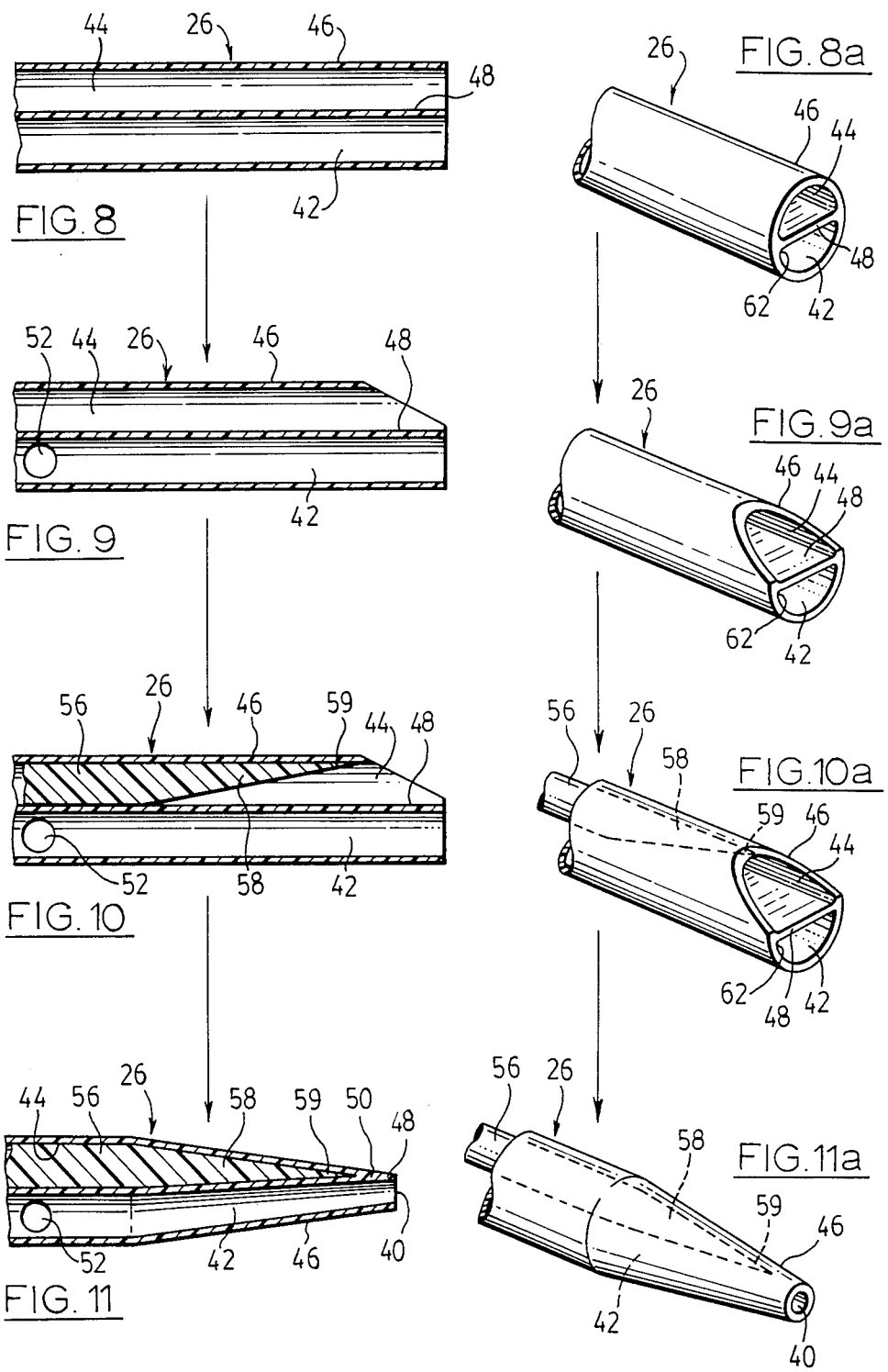

DUAL LUMEN CANNULA

This invention relates to a dual lumen cannula for insertion into a subclavian femoral or jugular vein of a patient to facilitate haemodialysis treatment. The invention also relates to procedures for manufacturing different parts of the dual lumen cannula.

It has been found desirable to produce dual lumen cannulas for use in subclavian or femoral vein insertion from a flexible extrusion defining both extraction and return lumens. The leading portion of such a cannula should be stiff enough and shaped to facilitate insertion yet retain some flexibility. The geometry and materials of the cannula should not affect operation of the cannula and should not unduly restrict blood flow in any way. In addition, the cannula should produce minimum blood damage to facilitate prolonged and safe operation. Such a cannula should also be simple and economical to manufacture for general use in haemodialysis.

A further consideration is the attachment of tubes to the two lumens of the cannula. Any discontinuity of internal profile at the joints or sharp bends can cause turbulent blood flow which can result in blood damage.

Returning to the leading end, this is usually tapered to facilitate insertion. An example of this is disclosed in U.S. Pat. No. 4,451,252. One problem with such tapering is because internal dead spaces must be avoided to prevent blood stagnation, it is difficult to produce a leading end which is not off-centered from the axis of the cannula. Such an offset and structure can result in insertion problems.

An object of the present invention is to provide an improved dual lumen cannula which overcomes or mitigates the aforementioned disadvantages of this type of cannula.

According to one aspect of the present invention there is provided a dual lumen cannula for insertion into the vein of a patient comprising a flexible elongate tubular portion consisting of an outer wall and by an integral septum dividing the tubular portion into extraction and return lumens, the extraction and return lumens being adapted to be connected at the proximal end of the portion to respective extraction and return tubes, the cannula having a generally conical leading end for insertion, the outer wall of the leading end being integral with the tubular wall tapering to define a return aperture communicating with the return lumen, the septum and the tubular wall of the conical leading end converging at a location just short of the return aperture to blank off the extraction lumen, and an insert located between the converging location and an extraction aperture in the tubular wall, the insert shaped to fill the extraction lumen to minimise blood flow in the extraction lumen downstream of the blood extraction aperture.

In a preferred embodiment of the invention the cannula is circular in cross-section, and the insert is made of polyurethane.

According to another aspect of the present invention there is provided a method of manufacturing the dual lumen cannula.

These and other aspects of the present invention will become apparent from the following description in combination with the accompanying drawings in which:

FIG. 1 is a diagrammatic view of a preferred embodiment of a dual lumen cannula according to the invention inserted in a patient;

FIG. 2 is a diagrammatic perspective view of the dual lumen cannula drawn to a larger scale than that used for FIG. 1;

FIG. 3 is an enlarged sectional view of the distal end of the cannula;

Figure 12:
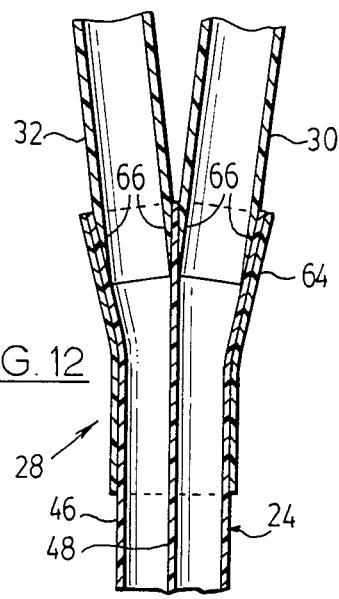

FIGS. 4, 5 and 6 are enlarged and sectional views taken on the lines 4—4, 5—5 and 6—6 of FIG. 2; respectively FIG. 7 is an end view of the cannula looking from the right of FIG. 3;

FIGS. 8, 8a, 9, 9a, 10, 10a and 11, 11a are respective sectional side and perspective views of a leading portion of the cannula at various stages in the process of manufacturing a conical tip on the cannula;

FIG. 12 is a longitudal partly sectional view of a Y-shaped portion shown in FIG. 2 drawn to the larger scale and illustrating here the return and extraction tubes arranged in the Y-shaped portion; and FIGS. 13a, 13b, 13c and 13d are diagrammatic perspective views of an end of the cannula showing the various steps in the manufacture of the Y-shaped connecting portion.

Reference is made first to FIG. 1 which illustrates a dual lumen cannula, generally indicated by reference numeral 20, according to a preferred embodiment of the invention, and shown with a patient receiving subclavian haemodialysis treatment.

The cannula is secured to a conventional dressing 22 by wing tabs 23 and the dressing, in turn, is secured to the skin of the patient. As shown, the cannula passes through the dressing and as can be seen in dotted outline, a flexible cylindrical portion 24 of a polyurethane extrusion is inserted into the subclavian vein. The cannula has a generally conical leading end 26 which will be described in greater detail later. The other end of the cylindrical portion 24 is a generally Y-shaped portion 28, which protrudes outwardly from and is secured by dressing 22. Extraction and return tubes 30, 32 are attached to the Y-shaped portion as will also be described in detail later.

FIG. 2 shows the cannula 20 in greater detail. The cylindrical portion 24 has at its proximal end the generally Y-shaped portion 28 for receiving the blood extraction and return tubes 30, 32. These tubes terminate at their outer ends in respective male luer fittings 34 for connection to complementary female luer fittings and carry closure clamps 33 (one of which is shown). Wing tabs 23 (sometimes known as suture wings) are formed integrally with a central tubular portion 38 which can rotate on the cylindrical portion 24 so that the catheter can be rotated in the portion 24. This rotation is sometimes necessary after insertion to re-orient the intake side holes if they happen to be occluded by engagement with the wall of the vein As better seen in FIG. 3, the leading end 26 is arranged to facilitate insertion of the cannula and it terminates in a centrally located circular return outlet 40 which communicates with a blood return lumen 42.

As also seen in FIG. 3, the leading end 26 tapers conically towards the outlet 40. The return and extraction lumens 42 and 44 respectively are defined between an outer wall 46 of the extrusion and a septum 48 which is integral with the wall, as best shown in FIG. 4. The septum 48 and the outer wall 46 converge at an integral portion 50 seen in FIGS. 3 and 6 just short of the return outlet 40 thus blanking off the extraction lumen 44.

The outer wall 46 is perforated by outlet openings 52 (one of which is shown) for facilitating returning blood from the lumen 42, and by openings 54 (one of which is shown) in the extraction lumen 44 to permit blood flow from the vein into this lumen. The opening 54 is positioned as close as possible to an insert 56 (to be described) to prevent dead spaces at a proximal end 60 of the insert where blood may clot.

The insert 56 is contained in the end of the cannula and is preferably the same thermoplastic material as that used for the cannula body. The shape of the insert is such that it fills the space at the leading end of the lumen 44. The insert has a tapered leading portion 58 for purposes which will be described. The insert 56 is made quite stiff to assist in making the conical shape of the leading end 26 as will be described. The proximal end 60 of the insert terminates just short of the inlet opening 54 and is obliquely cut to minimize turbulence when blood is drawn into the lumen 44 through the inlet opening.

Reference is now made to FIG. 4 which is a cross-sectional view of the cannula taken in the line 4—4 of FIG. 3. As seen in this view the outer wall 46 and integral septum 48 combine to divide the cross-section into the two similar lumens 42, 44. The main part of the insert 56 is shaped to fit snugly in the lumen so that blood cannot leak towards the leading end where the blood would stagnate and clot. It will also be seen that the septum 48 blends into the wall 46 at curved portions 62 to also avoid blood stagnation.

As seen in FIG. 5, the extraction lumen 44 and leading portion 58 of the insert have been reduced in cross-sectional area toward the return outlet 40, and the lumen 42 though changed from the shape shown in FIG. 4 continues to permit return blood flow. Turning now to FIG. 6, the septum and outer wall have been brought together to form the integral portion 50 which of course has a thicker cross-section than that of the wall 46 alone.

From FIG. 7 it will be seen that the outlet 40 is circular and is defined essentially by the conical surface of the leading end 26 which merges smoothly with the exterior of portion 24, to facilitate insertion of the cannula.

Reference is now made to FIGS. 8, 8a, 9, 9a, 10, 10a and 11, 11a to describe the manufacture of the leading end 26. The end of the extrusion shown in FIGS. 8, 8a is first cut obliquely towards its end so that a portion of the wall 46 of the extraction lumen is removed to expose the septum 48 as shown in FIGS. 9, 9a. As shown in FIGS. 10, 10a the flexible insert 56 is then positioned in the extraction lumen. This insert fills the lumen 44 and its leading portion 58 tapers from the septum 48 towards the wall 46 and is adjusted so that its tip 59 terminates just inside the outer wall 46. The leading end of the tube with the insert in place is pushed into a heated die which has an internal shape corresponding to that of the desired shape of the cannula shown in previous FIG. 5. Because of the heat, the tube and insert soften and there will be bonding as surfaces are forced together and the leading portion 58 will be deflected towards the septum 48 to result in the leading end 26 of the shape shown in FIGS. 11, 11a. The leading end 26 is then generally conical, centred on the axis of the cannula, and blends smoothly into the portion 24 of the cannula upstream from the portion 58 of the insert.

The shaped leading end the septum and the conical wall converge at the integral portion 50 just short of the end and the circular return outlet 40 is formed to communicate with the return lumen. It will be appreciated tha the strength of the portion 58 aids in causing the extrusion to deform into the conical leading end 26 with its axis centred. Because of the materials used for the insert 56 and portion 24, bonding also occurs between the insert and the walls and septum of the tube so that the insert remains fixed in the position shown in FIG. 3.

It will thus be appreciated that the centred conical leading end 26 as shown in FIG. 11a will facilitate insertion of the cannula as it slides over a conventional guide wire. Also, the cannula has increased stiffness due to the insert 56 to minimise the risk of collapse of the leading end portion of the cannula during use.

The structure of the Y-shaped portion 28 will now be described with reference firstly to FIG. 12 of the drawings which is a sectional view of the Y-shaped portion 28 shown in FIG. 2. The outer wall 46 and septum 48 are deformed to shape the generally Y-shaped portion and a heat-shrunk sleeve 64 is mounted thereon to strengthen the structure, by a method as will be described. The Y-shaped portion receives the extraction and return tubes 30 and 32, the ends 66 of which are tapered so that when bonded into the respective openings of the Y-shaped portion the interior surfaces of the tubes 30 and 32 blend smoothly with the interior walls of the proximal ends of the lumens 42 and 44 respectively. This arrangement ensures that there is minimal disruption to blood as it flows between the lumens and the respective tubes so that haemolysis is minimized.

Figure 13A:
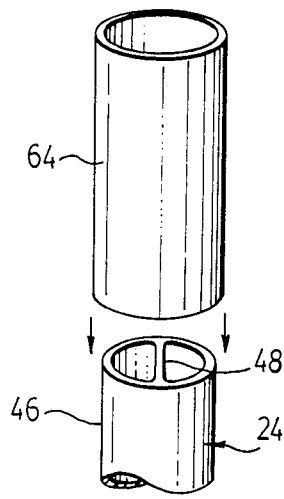
Figures 13B, 13C, 13D:
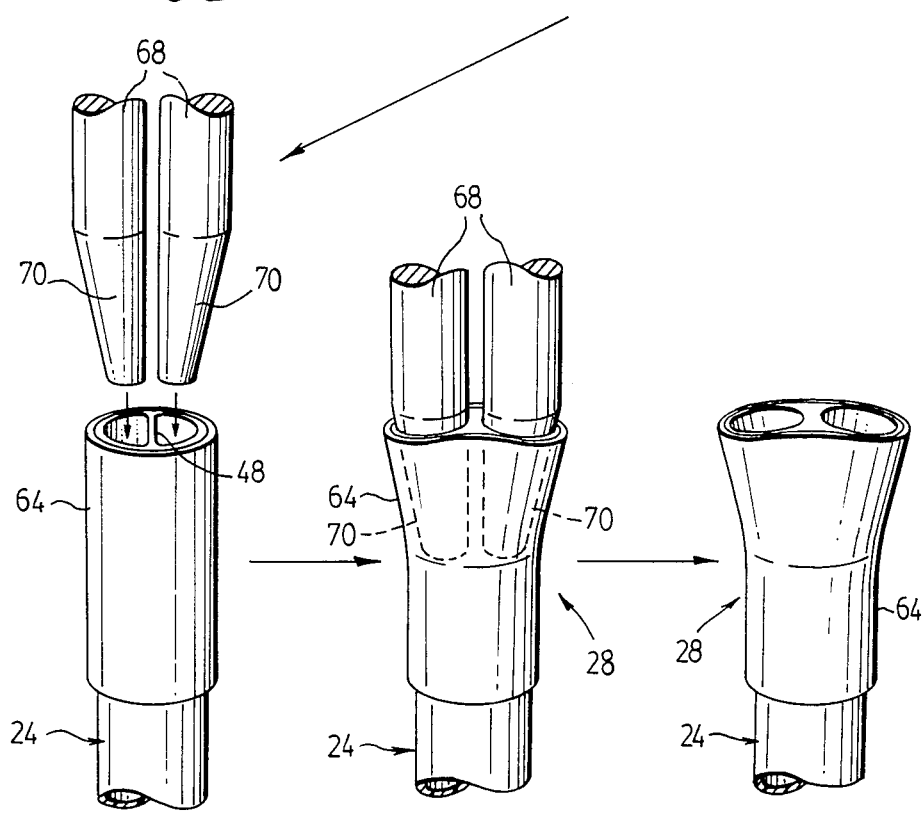

The manufacture of the Y-shaped portion shown in FIG. 12 will now be described with reference to FIGS. 13a, 13b, 13c and 13d respectively. As shown in FIG. 13a, manufacture commenced by placing sleeve 64 on the extrusion and then heat shrinking the sleeve in position as shown in FIG. 13b. The sleeve 64 strengthens the end of the cannula for receiving the tubes 30, 32. In order to make the Y-shaped portion 28, mandrels 68 having generally conically shaped ends 70, are heated and the ends then inserted into respective lumens as shown in FIG. 13c. The tube deforms around the conical ends to conform to the conical ends and after a predetermined time to let the tube and collar material set, the mandrels are removed and the Y-shaped portion 28 remains set as shown in FIG. 13d. The cylindrical portion 24 can then receive the tubes 30 and 32 with the tapered ends 66 bonded in place as shown in FIG. 12. The tapering is such that the ends are very thin and this minimises turbulence and resulting blood damage.

It will be appreciated that various modifications may be made to the cannula, and to the processes for making parts of the cannula as described without departing from the scope of the invention. For example, although the extrusion is made of polyurethane and the insert of polyethylene it will be appreciate that these could be made of any other material having similar properties which are suitable for use in the processes described above. Also, although the cannula has been described in use in a subclavian vein it will also be appreciated that it can be used in both femoral and jugular veins. It will also be appreciated that to facilitate insertion a flexible obturator can be used inside the return lumen or intake lumen and after insertion the obturator is withdrawn in the usual way. Similarly, the cannula can be used in other locations for other purposes.

I claim:

1. A dual lumen cannula comprising:
a flexible elongate tubular portion consisting of a tubular wall separated by an integral septum into similar extraction and return lumens, the cannula having a generally tapered leading end to facilitate insertion and blood extraction and blood return openings communicating with respective extraction and return lumens in proximity to the leading end, the extraction and return lumens terminating at an other end of the tubular portion at similar conically-shaped inner surfaces, each inner surface adapted to receive ends of respective blood extraction and blood return tubes, each said end of the tubes having a generally conically shaped outer surface and the walls of each end narrowing towards a tip which has minimal wall thickness so that the interiors of the respective tubes and lumens form substantially smooth surfaces to minimize blood damage.

2. A dual lumen cannula as claimed in claim 1 in which the lumens have a D-shaped cross section.

3. A dual lumen cannula as claimed in claim 1 in which the cannula has a conical leading end, the outer wall of the leading end being continous with the tubular wall and tapering to define a return aperture centered on the axis of the cannula and communicating with the return lumen, the septum and the tubular wall of the conical leading end converging at a location just short of the return aperture to blank off the extraction lumen, and an insert contained within the extraction lumen and located between said location and extraction aperture in the tubular wall, the insert being shaped to fill the extraction lumen between said location and the blocked extraction aperture.

* * * * *